US00PP23092P3

(12) United States Plant Patent
Sykes

(10) Patent No.: US PP23,092 P3
(45) Date of Patent: Oct. 2, 2012

(54) MANDARIN TREE NAMED 'MERBEINGOLD 2350'

(50) Latin Name: ***Citrus reticulata*×(*C. reticulata*×*C. sinensis*)**
Varietal Denomination: Merbeingold 2350

(75) Inventor: Stephen Richard Sykes, Mildura (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 12/927,657

(22) Filed: Nov. 19, 2010

(65) Prior Publication Data

US 2011/0107481 P1 May 5, 2011

Related U.S. Application Data

(63) Continuation of application No. 11/729,049, filed on Mar. 27, 2007, now abandoned.

(30) Foreign Application Priority Data

Oct. 16, 2006 (QZ) ..... PBR 2006278

(51) Int. Cl.
*A01H 5/00* (2006.01)

(52) U.S. Cl. ..... Plt./202

(58) Field of Classification Search ..... Plt./202
See application file for complete search history.

(56) References Cited

U.S. PATENT DOCUMENTS

| | | | |
|---|---|---|---|
| 2008/0127378 | P1 | 5/2008 | Sykes |
| 2008/0127379 | P1 | 5/2008 | Sykes |
| 2011/0778836 | | 3/2011 | Sykes |

OTHER PUBLICATIONS

Acceptance of Merbeingold 2350, Application No. 2006/278, for Plant's Breeder's Right Registration on Dec. 1, 2006. Published in Plant Varieties Journal, 2007 19(4), Canberra: Australian Government Publishing Service, Australia.
Complete file history for U.S. Patent Publication No. 2008-0127379 P1, published May 29, 2008 (Stephen Richard Sykes) (issued from U.S. Appl. No. 11/729,049).

*Primary Examiner* — Annette Para
(74) *Attorney, Agent, or Firm* — John P. White; Cooper & Dunham LLP

(57) ABSTRACT

'Merbeingold 2350' is a new Australian variety of mandarin. It was selected from the progeny obtained following a controlled pollination of 'Imperial' mandarin×'Ellendale' tangor in 1984. It was selected because it is strongly parthenocarpic and is capable of yielding seedless fruits, which are sweet, juicy and easy-to-peel. Fruit maturity is mid season in the Murray Valley of Australia. The rind of Merbeingold is thin, orange-to-orange red, strong yet easily peeled. Its fruits can be snap picked, eliminating a need to clip. Internally, the flesh of 'Merbeingold 2350' is attractive, orange in colour and juicy with a good sugar/acid balance.

5 Drawing Sheets

Latin name of the genus and species of the plant claimed: *Citrus reticulata*×(*C. reticulata*×*C. sinensis*)

Variety denomination: 'Merbeingold 2350'.

This application is a continuation of U.S. plant application Ser. No. 11/729,049, filed Mar. 27, 2007, now abandoned claiming priority of Australian Breeder's Right Application No. 2006/278, filed Oct. 16, 2006 the contents of all of which are hereby incorporated by reference.

'Merbeingold 2350' was accepted for Plant Breeder's Right ("PBR") registration on Dec. 1, 2006 when a provisional PBR was granted. Acceptance was published in the Plant Varieties Journal (2007) Vol. 19, No 4, p23 (see, ipaustralia.gov.au/pdfs/plantbreed/PVJ_19_4.pdf). The Commonwealth of Australia Plant Breeder's Rights Act 1994 follows the guidelines of the International Convention for the Protection of New Varieties of Plants—UPOV Convention (1961), as revised at Geneva (1972, 1978 and 1991). Australia is a UPOV Member State.

BACKGROUND OF THE INVENTION

'Merbeingold 2350' is a new variety of mandarin (*Citrus* species) bred by CSIRO Plant Industry. A copending application, U.S. Ser. No. 11/729,003, has been made for the variety 'Merbeingold 2336', which is a sibling selected from the same family as 'Merbeingold 2350'.

'Merbeingold 2350' is a mandarin variety selected from a family produced by making a controlled cross between 'Imperial' mandarin (seed parent) with 'Ellendale' tangor (pollen parent). Thus, the botanical name for the plant is:

*Citrus reticulata*×(*C. reticulata*×*C. sinensis*)

The plant may be used for horticultural production of mandarin fruits.

The plant was asexually reproduced in South Australia, Australia.

'Merbeingold 2350' was selected from a family of 241 hybrids generated by a controlled cross-pollination of 'Imperial' mandarin (maternal parent) with 'Ellendale' tangor (pollen parent).

'Imperial' mandarin (unpatented) is an Australian variety that originated at Emu Plains, NSW, as a chance seedling in 1890. It is possibly a hybrid of the 'Mediterranean' mandarin. 'Imperial' trees are vigorous, upright and of medium size and they yield fruits that are early maturing.

'Ellendale' tangor (unpatented) is another Australian variety that was discovered as a chance seedling at Burrum, Queensland in 1878. Although its parentage is unknown, its characteristics and fruit size indicate that it is a tangor (mandarin×orange cross). 'Ellendale' trees are generally large and of a spreading-round habit and produce large mid-to-late season fruit depending on where they are grown.

The seediness of fruits from both 'Imperial' and 'Ellendale' can be variable ranging from many-to-few-to-zero depending on the proximity of other sources of pollen. Both varieties are capable of producing fruits parthenocarpically.

CSIRO Plant Industry crossed 'Imperial' with 'Ellendale' to combine the characteristics of the two varieties and generate new parthenocarpic hybrids for selection of potential new varieties of seedless mandarins.

The controlled cross-pollination was conducted by emasculating an un-opened flower bud of the maternal parent and applying pollen from the paternal parent to the receptive stigma using a sterile soft-haired paintbrush. Pollen of 'Ellendale' tangor was collected by drying anthers, which had been removed from unopened flower buds, in Petri dishes over silica gel in a dessicator. Dried dehisced anthers were stored in sealed glass vials over silica gel at 4° C. until needed. The cross was made in 1984 and the resultant seeds were extracted from fruits in 1985 and sown in a standard seed bed under glasshouse conditions. Emergent seedlings were transferred to a standard potting mix in pots and maintained under glasshouse conditions until they were rowed out in the breeding orchard at a planting density of 2 m within and 6 m between rows. Hybrid seedlings were maintained under irrigated orchard conditions thereafter. Standard citrus cultivation techniques were used to maintain the trees including application of fertilisers.

When hybrid 2350 flowered, it was subjected to a range of pollination treatments to assess its potential for producing seedless fruits. Fruits were harvested over 4 years and assessed for fruit quality, Based on the data collected, hybrid 2350 was selected for entry into second phase evaluation trials.

The selection was entered into a comparative trial at CSIRO Plant Industry Koorlong (NW Victoria). Trees of hybrid 2350 and 4 comparator varieties (viz. 'Clementine Nules', 'Imperial' mandarin, 'Ellendale' tangor, and 'Merbeingold 2336') were propagated by budding to 3 rootstocks (viz. 'Carrizo' citrange, 'Cleopatra' mandarin and 'Symons' sweet orange) in the nursery at CSIRO. The DUS trial was planted during spring 2001. The soil type was classified as being Tiltao sand (Northcote, K.H. 1951. A Pedological Study of the Soils Occurring at Coomealla, New South Wales, Commonwealth Scientific and Industrial Research Organisation, Melbourne, Australia). The trees were irrigated by overhead sprays and fertilised using a standard citrus N:P:K (12:3:3) formulation. Fertiliser was applied to young trees at 2-monthly intervals and to trees 2 years and older at six-monthly intervals at a rate such that they received 800 kg/ha/year. Trace elements, primarily manganese and zinc were applied as foliar sprays as required. The trial was embedded within a larger trial that compared other selections from CSIRO's citrus breeding program. The trial was laid out as two randomized blocks with a three-tree plot for every scion/rootstock combination within each block. Rootstocks were randomized within plots. Trees were maintained vegetatively for the first three years and allowed to retain fruits from season 2004-05 onwards.

Comparative data for quantitative fruit characteristics were collected in seasons 2006 and 2007. Spring-flush leaves were sampled from trees during January 2007.

Hybrid 2350 was also entered along with other selections into regional test plots with anonymous cooperating citrus growers under confidential testing agreement arrangements to protect inherent intellectual property. Based on its performance in these trials and test plots, hybrid 2350 was named 'Merbeingold 2350'.

Daughter trees of 'Merbeingold 2350' propagated from the original seedling tree by asexual or vegetative means are uniform and stable. Similarly grand-daughter trees are uniform and stable. Trees of 'Merbeingold 2350' have been propagated by grafting or budding to seedling rootstocks, by top-working to established orchard trees and by rooting cuttings, confirming its uniformity and stability.

SUMMARY OF THE INVENTION

Fruits of 'Merbeingold 2350' have the capacity to be seedless and seed numbers are dependent on cross-pollination. In regional test plots, mean seed numbers have ranged from less than 1 up to 10 seeds per fruit. Low seed numbers have occurred where trees are planted close to navel oranges, which because they are pollen sterile, cannot cross-pollinate 'Merbeingold 2350's flowers. Under these circumstances, seedless and low-seeded fruits have been harvested. Where higher seed numbers have been recorded, trees of 'Merbeingold 2350' have been surrounded by strong pollen producers such as 'Valencia' orange, 'Murcott' tangor and 'Minneola' tangelo. In these situations, cross-pollination is promoted and seedier fruits result. Clearly, successful adoption of 'Merbeingold 2350' to produce seedless and low-seeded fruits will depend on its location with regard to potential cross-pollinator varieties. In orchards where seed numbers have been one-or-less per fruit, a large proportion of the fruits have been seedless.

The rind is thin and the fruits are easy-to-peel leaving segments free of albedo tissue. The segments are readily separated without breaking and are tender with soft walls resulting in a pleasant texture when eaten. The rind, though thin, is strong giving a robust intact fruit suggesting it will ship well and be suited for export.

The juice is sweet with a ° Brix of around 11-12. With an acid concentration of 1% or just under at maturity, fruits of 'Merbeingold 2350' have a pleasant sweet flavour. The juice does not have an overly distinctive flavour.

The rind is an attractive red-orange which should have high appeal in the market place. In this regard, the fruit has been compared to the variety Nova but it does not appear to suffer granulation like Nova. The colour of the flesh, like 'Clementine Nules' and 'Ellendale' is medium orange. The flesh of 'Imperial' is yellow orange. As stated above, the colour of the rind is orange-red, while the colour of the rinds of 'Clementine Nules' and 'Ellendale' is medium orange, and the rind of 'Imperial' is yellow orange. The color of the albedo is white like each of 'Clementine Nules', 'Ellendale', and 'Imperial'.

Fruits of 'Merbeingold 2350' can be snapped from the tree leaving the button intact. They reach maturity during the period late June-through-August in Australia's Murray Valley depending on soil type, rootstock and season. Fruit size is good with mean fruit weights in the range 120-140 g.

DETAILED BOTANICAL DESCRIPTION OF THE PLANT

Variety—'Merbeingold 2350'

*Citrus reticulata*×(*C. reticulata*×*C. sinensis*)

Figure 1A:
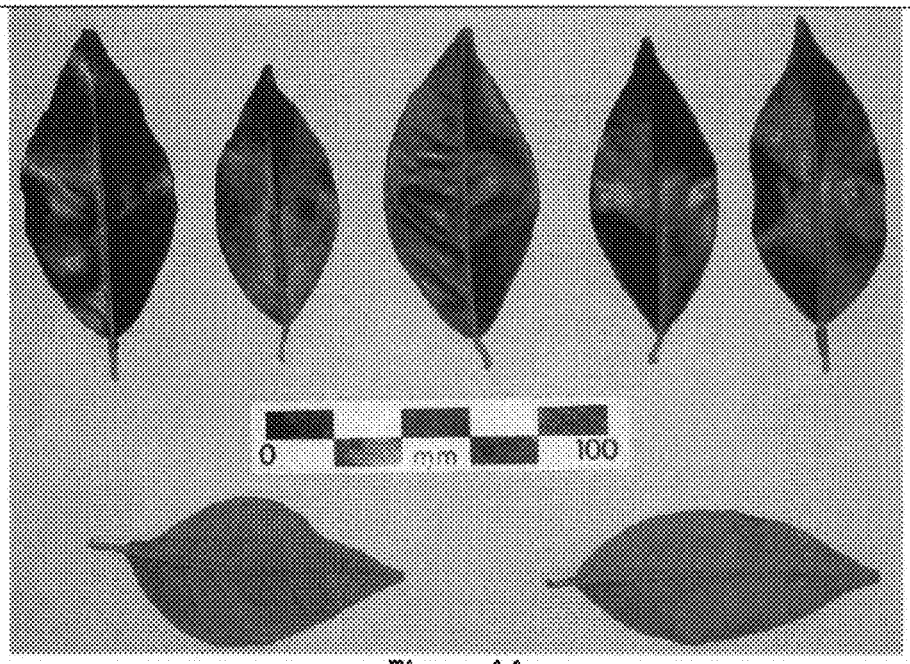
FIGS. 1A-1C: Show leaves from 'Merbeingold 2350' (FIG. 1A) and its parents, 'Imperial' mandarin (FIG. 1B) and 'Ellendale' tangor (FIG. 1C). In 'Merbeingold 2350' the Lamina length:width ratio=2.2±0.2; in 'Imperial' mandarin the Lamina length:width ratio=2.7±0.2; and in 'Ellendale' tangor the Lamina length:width ratio=2.1±0.2
Figure 1B:
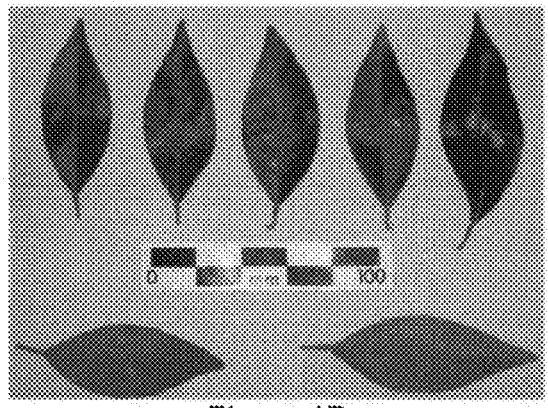
Figure 1C:
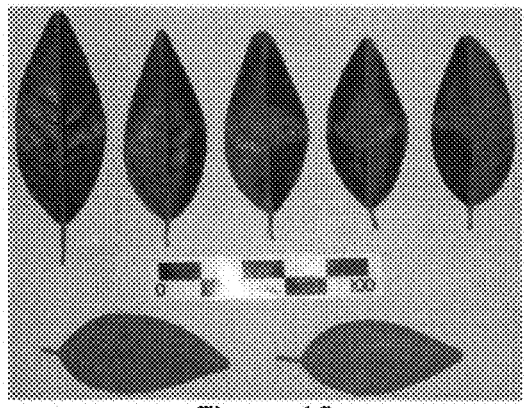
Figure 2A:
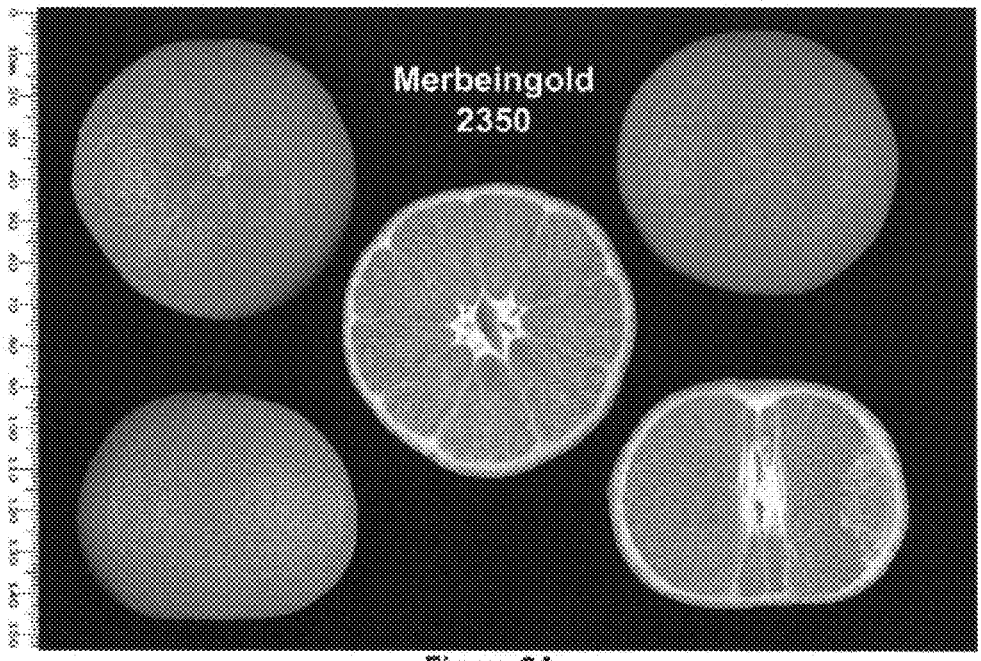
FIGS. 2A-2C: Show fruit of 'Merbeingold 2350' (FIG. 2A) and its parents, 'Imperial' mandarin (FIG. 2B) and 'Ellendale' tangor (FIG. 2C).
Figure 2B:
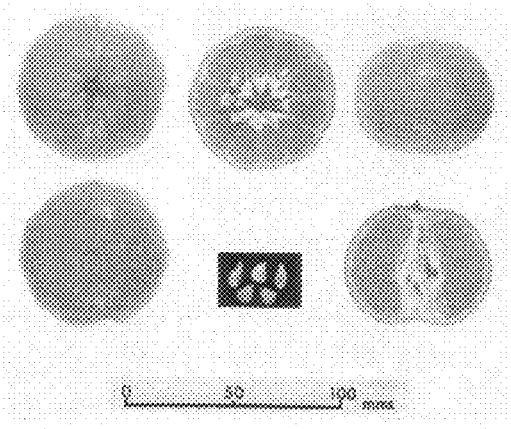
Figure 2C:
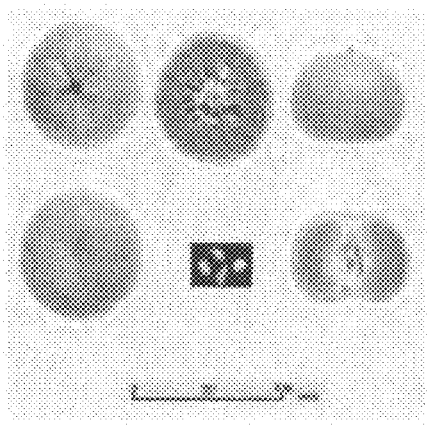

Descriptors used herein from 1) European Union Community Plant Variety Office, Protocol for distinctness, uniformity and stability tests. *Citrus* L.—Group 1 MANDARINS. CPVO-TP\201\1 Adopted 18 Nov. 2004, and 2) IPGRI (1999) Descriptors for Citrus. International Plant Genetic Resources Institute, Rome, Italy (ISBN 92-9043-425-2).

Plant:

Diploid, growth habit spreading-to-upright, tree shape spheroid-ellipsoid, density of branches medium, branch angle narrow, trunk surface smooth, shoot tip green and surface glabrous. Branch size at the crotch of the tree, and elsewhere for that matter, is understandably variable, but the angle of branching is consistent with a mean of 38.2 mm±2.6 mm. Crotch angles were measured for a number of trees on the 3 rootstocks ('Carrizo' citrange, 'Symons' sweet orange and 'Cleopatra' mandarin) with branch thickness ranging from around 25-to-75 mm. The branching angle was consistent on smaller branches distal to the trees crotch. Compared to the varieties 'Clementine Nules', 'Ellendale', and 'Imperial', the tree has a spreading growth habit, like 'Ellendale', but unlike 'Clementine Nules' which has a drooping growth habit, and 'Imperial' which has an upright growth habit. Additionally, the tree has very short spines, compared to 'Clementine Nules', 'Ellendale', and 'Imperial', which each have short spines.

The height and spread of 3 trees of 'Merbeingold 2350' were measured. These trees had been planted as nursery-propagated trees (12 months from budding) in April 2000 and were 12 years-old when measured. Intra- and inter-row spacing was 2 m and 6 m, respectively. North-south and east-west diameters of the 'Merbeingold 2350' trees ranged from 3000-to-3600 mm and 3100-to-3400 mm, respectively. Their height ranged between 3300-to-3800 mm. The Royal Horticultural Society (R.H.S.) colour chart data provided herein were collected from the same trees used for height and spread measurement.

Figure 3:
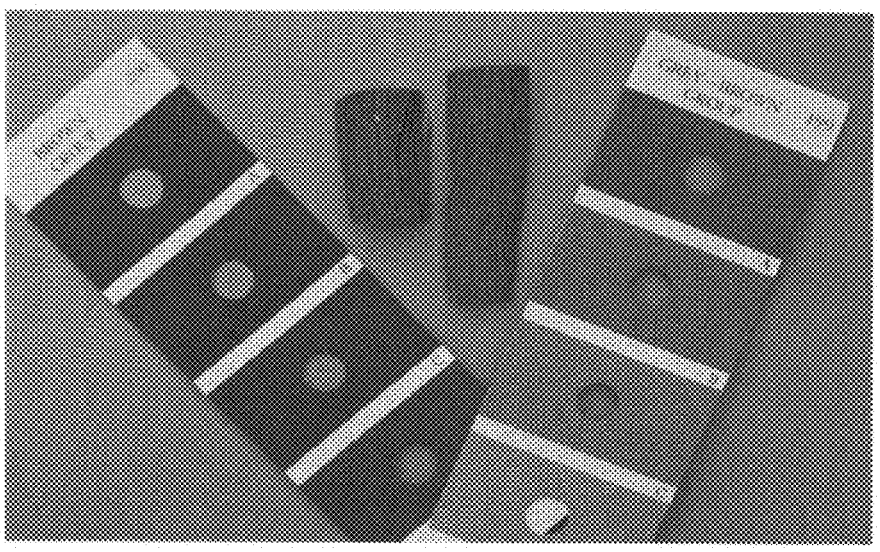
FIG. 3: A. Shows the colour of bark of the 'Merbeingold 2350' tree. B. Shows the colour of leaves of the 'Merbeingold 2350' tree. C. Shows the colour of fruit of the 'Merbeingold 2350' tree.
Figure 3:
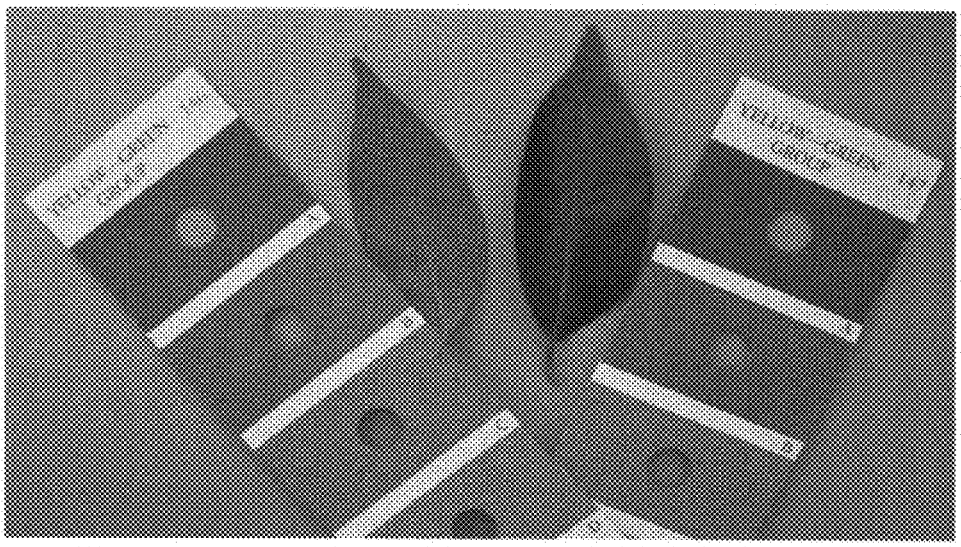
Figure 3:
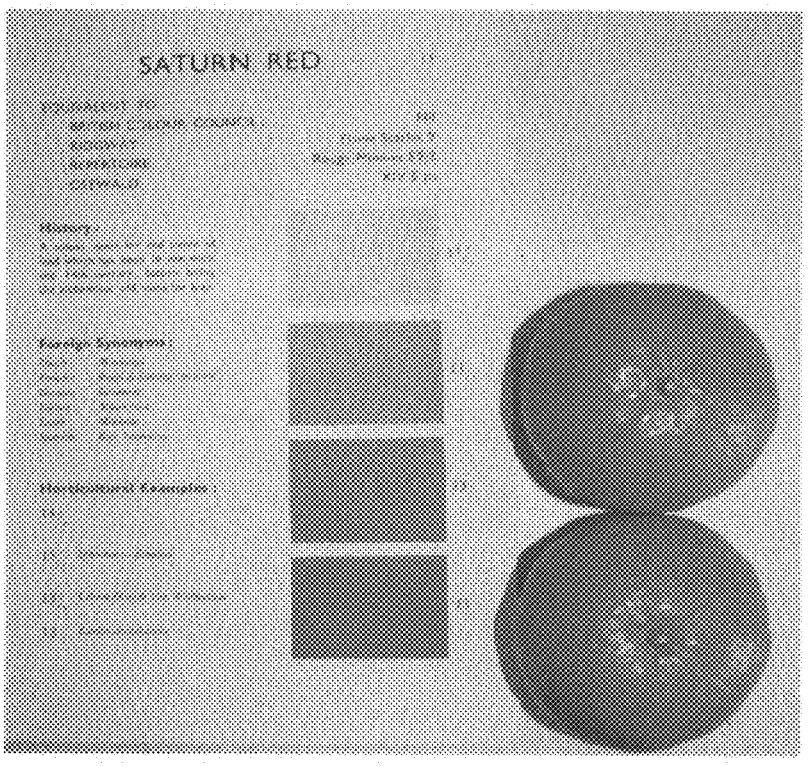
Figure 4:
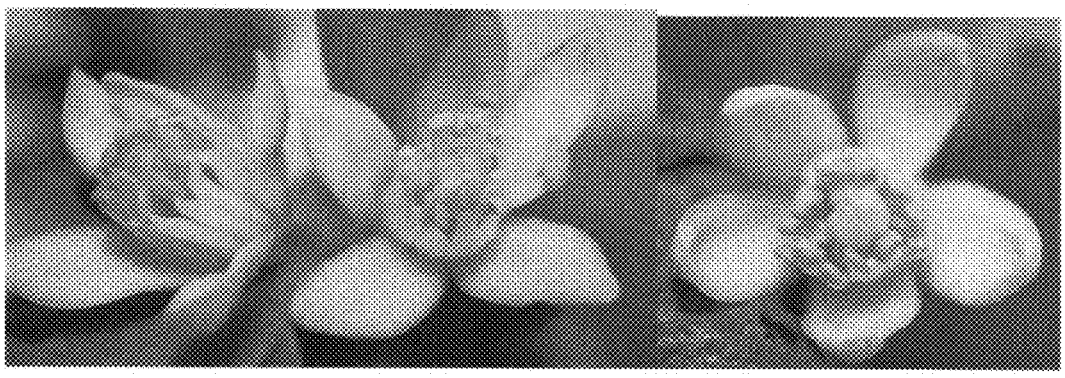
FIG. 4: Shows flowers of the 'Merbeingold 2350' tree.

Bark samples were removed from a central leader within the canopy and colour scored away from the tree under conditions suggested by the R.H.S. colour chart document. The bark was streaked as shown in FIG. 3A and was thus scored as being brown-grey (200) to grey brown (199) with bands represented by these colour types.

Spine (thorn):

Either absent or very sparse on adult tree, length on adult tree short <5 mm, shape straight.

Leaf:

Evergreen, type simple, shape ovate, intensity of green colour on lamina medium-to-dark, colour variegation absent, margin very weakly dentate-to-mostly entire, shape of apex acute, lamina length medium (85±8 mm), lamina width narrow-to-medium (39±3 mm), lamina length to width ratio 2.2±0.2, cross-sectional shape intermediate, lamina undulation absent-to-very slight, lamina attachment brevipetiolate, petiole length short (10±3 mm), petiole wings obdeltate and very narrow, petiole attachment to stem curved, junction between petiole and lamina articulate, colour of lamina upper/lower surface same. The colour of the leaves may be characterized as dark to very dark green, like the 'Clementine Nules', 'Ellendale', and 'Imperial' varieties.

The upper (adaxial) surface of the 'Merbeingold 2350' leaf was scored as 147a from the yellow-green group; the lower (abaxial) surface was scored as 146a from the yellow-green group of the R.H.S. colour chart (FIG. 3B).

Flower:

Hermaphrodite, arrangement solitary and as a raceme, position axillary and terminal, length of petal short-to-medium, anther colour medium yellow, viable pollen sparse-to-normal, length of anther relative to style shorter (inferior), colour of open flower white like the 'Clementine Nules', 'Ellendale', and 'Imperial' varieties, 5 petals per flower, stamens>4 per petal, style straight and complete, self-compatible.

Fruit:

Maturity mid-season (late June-August, Australia), borne both inside and outside canopy, obloid, attachment to stalk medium-to-strong, broadest at equator, shape in transverse section circular, base flattened-to-slightly concave, apex flat-to-truncate, neck absent, slight depression at stalk end, number of radial grooves at stalk end intermediate, collar absent, distal part flattened, no depression at distal end, areola absent, stylar end closed, stylar scar small, style not persistent, navel opening absent, radial grooves at distal end absent, rind surface predominantly orange-to-orange red, surface glossiness strong, surface roughness medium, rind smooth to slightly pitted, oil glands all more-or-less same size, pitting of oil glands present pebbling absent, oil glands conspicuous, small and of low density, rind thin (2-3. mm), rind adherence to flesh weak-to-medium, rind strength strong, rind oiliness medium, albedo white and loose, amount of albedo adhering to flesh very small, albedo strands absent, flesh medium-to-dark orange, pulp colour uniform, pulp firmness intermediate, pulp texture fleshy, core small-to-medium, round and sparsely filled, segments uniform, rudimentary segments absent, number of well developed segments medium (5-to-10; mean 9.1±0.7), adherence of segment walls to each other medium, strength of segment walls medium, vesicle length long, vesicle thickness medium-to-thin, navel absent, juiciness high, soluble solids medium-to-high 9-15° Brix, acidity medium, strength of fibre medium, parthenocarpy present.

The colour of the rind of fruit from the 'Merbeingold 2350' tree is Saturn Red 13-13/1 in the R.H.S. colour chart (FIG. 3C).

It will be understood that the average size of fruits will vary with location, season, rootstock, nutrition, irrigation, crop load etc. The data provided in Table 1 are for the 'Merbeingold 2350' tree grown in a semi-commercial planting. The trees were top-worked in January 2006 in Australia.

Fruit weight and diameter of 'Merbeingold 2350' fruit determined from a random sample of fruit taken from a fruit bin at harvest of top-worked trees in the semi-commercial sized trial. Data are means ± standard deviations for sample sizes that varied according to year.

| Variety | Harvest date | Fruit weight (g) | Fruit diameter (mm) |
|---|---|---|---|
| Merbeingold 2350 | Jun. 12, 2008 | 108.8 ± 5.5 | 64.8 ± 2.3 |
| | Jul. 29, 2009 | 87.5 ± 32.0 | 56.8 ± 8.9 |
| | Jul. 21, 2010 | 158.4 ± 29.2 | |
| | Jul. 22, 2011 | 101.5 ± 25.3 | 61.7 ± 6.0 |

Missing values are where these data were not recorded.

Seed:

Number of seeds under controlled manual self pollination few (0-4), 0-to-15 under open pollination depending on proximity of other pollen sources, monoembryonic, shape ovoid, length short, width narrow, surface smooth, external colour whitish/cream, colour of inner seed coat light brown, chalazal cream, cotyledons white-to-light yellow-cream.

Seed size and dimension:

| | Length (mm) | Width (mm) | Breath (mm) | 1/Width | 1/Breadth |
|---|---|---|---|---|---|
| Mean | 10.32 | 4.51 | 5.7 | 2.30 | 1.82 |
| Std. Dev. | 0.74 | 0.38 | 0.40 | 0.21 | 0.20 |

The invention claimed is:

1. A new and distinct parthenocarpic mandarin tree named 'Merbeingold 2350' as illustrated and described.

* * * * *

A

B

C